United States Patent [19]
Redlinger

[11] Patent Number: 6,146,650
[45] Date of Patent: Nov. 14, 2000

[54] MOISTURIZING SKIN CREAM

[75] Inventor: Rita Redlinger, San Diego, Calif.

[73] Assignee: Sun-Pro of California, Inc., San Diego, Calif.

[21] Appl. No.: 09/499,572

[22] Filed: Feb. 7, 2000

[51] Int. Cl.[7] .............................. A61K 6/00; A61K 9/127
[52] U.S. Cl. ........................... 424/401; 424/450; 514/847
[58] Field of Search ................................... 424/401, 450; 514/847

[56] References Cited

U.S. PATENT DOCUMENTS 4,883,359  11/1989  Goodman et al. ......................... 424/78
6,013,270   1/2000  Hargraves et al. ...................... 424/401

*Primary Examiner*—Thurman K. Page
*Assistant Examiner*—S. Tran

*Attorney, Agent, or Firm*—Nydegger & Associates

[57] ABSTRACT

The present invention is directed to a moisturizing skin cream that is safe and effective, and can be applied to all areas of the skin including the face and neck. The skin cream is specially formulated to deliver collagen, avocado oil, aloe and vital nutrients required by the skin such as vitamins A, C, D and E in specific proportions. Further, the skin cream of the present invention employs liposomes to effectively deliver the nutrients to the proper skin depth thereby improving the performance of the skin cream. The specially formulated vitamin composition can be combined with a standard base that may include emollients, lubricants, emulsifying agents, thickening agents, humectants, preservatives, antifungal agents, fragrances and wetting agents. When used as directed, the skin cream of the present invention effectively softens, moisturizes and provides needed nutrients to the skin, thus helping to prevent the premature aging of skin.

7 Claims, No Drawings

MOISTURIZING SKIN CREAM

FIELD OF THE INVENTION

The present invention pertains generally to a moisturizing skin cream. More particularly, the present invention pertains to a multi-purpose skin cream formulated to prevent the premature aging of skin. The present invention is particularly, but not exclusively, useful for a moisturizing skin cream suitable for use on the face and neck.

BACKGROUND OF THE INVENTION

The skin is the largest organ of the human body, primarily functioning to protect the body's internal organs from the outside environment. The outside environment that the skin must endure may consist of large fluctuations in both temperature and humidity. Further, the skin may be exposed to radiation from the sun or other sources. Additionally, the skin is routinely exposed to wind, dust, dirt and other harsh chemicals. Finally, the skin must survive the daily rituals that may include washing, shaving, and/or the application of cosmetics.

These environmental factors contribute to what is often referred to as the premature aging of skin. In particular, these environmental factors have been known to cause aging lines, wrinkles, skin dryness characterized by the loss of the skin's natural oils and moisture, skin fading, age spots, and the loss of skin elasticity.

In addition, it is known that proper skin nutrition, characterized by the adequate supply and consistent replenishment of certain vitamins to the skin can both reduce the effects that environmental factors have on the skin, and may also reverse the signs of premature skin aging. Further, it is known that improper skin nutrition due to a deficiency of certain vitamins can cause premature aging, even in the absence of other environmental factors.

Recently, widespread use of tretinoin creams such as Retin-A® have been made in an attempt to reverse the premature aging of skin. Some evidence shows tretinoin may improve fine wrinkling, mottled hyperpigment-action and roughness associated with photodamage. Unfortunately, tretinoin creams are toxic, thus requiring supervision by a doctor and a prescription. Further, tretinoins often cause unwanted side effects such as local inflammation, redness, scaling, and a slight stinging sensation. Still further, tretinoin patients must limit sun exposure during use. Another treatment that has seen recent use for the purpose of inhibiting premature aging are skin renewal acids such as alpha hydroxy acid. Although these renewal treatments may show some positive results in reversing the premature aging of skin, they are often accompanied by several unwanted side effects including dry skin and irritation. Further, renewal acid treatments are often criticized for producing results slowly.

In light of the above it is an object of the present invention to provide a safe and effective skin cream suitable for the purposes of softening the skin and preventing the premature aging of skin. It is another object of the present invention to provide a moisturizing skin cream that effectively delivers vitamins to the skin to ensure proper skin nutrition. It is yet another object of the present invention to provide a moisturizing skin cream suitable for application to the face and neck area. Yet another object of the present invention is to provide a moisturizing skin cream which is easy to use, relatively simple to manufacture, and comparatively cost effective.

SUMMARY OF THE PREFERRED EMBODIMENTS

The present invention is directed to a moisturizing skin cream that is safe and effective, and can be applied topically to all areas of the skin including the face and neck. For the purposes of the present invention, the skin cream is specially formulated to deliver collagen, avocado oil, aloe and vital nutrients required by the skin such as vitamins A, C, D and E, in specific proportions. Further, the skin cream of the present invention employs liposomes to effectively deliver the nutrients to the proper skin depth thereby improving the performance of the skin cream. The specially formulated vitamin composition and delivery system can be combined with a base that may include emollients, lubricants, emulsifying agents, thickening agents, humectants, preservatives, antifungal agents, fragrances and wetting agents. In the preferred embodiment, the base is an emulsion of oils and water having the following primary ingredients; about 52 percent deionized water, 10 percent petrolatum and 5 percent propylene glycol. When used as directed, the skin cream of the present invention effectively softens, moisturizes and provides collagen, avocado oil, aloe and a unique combination of needed nutrients to the skin. By effectively softening, moisturizing, and supplying appropriate vitamins to the skin, the skin cream of the present invention effectively helps to prevent the premature aging of skin.

DESCRIPTION OF THE PREFERRED EMBODIMENT

A skin cream in accordance with the present invention is shown in Table 1. Table 1 lists the ingredients and proportions of 5 embodiments of the present invention, designating the embodiments I, II, III, IV and V. Composition I shown in Table 1 is the preferred embodiment. The top portion of Table 1 shows the ingredients and proportions of the base, and the bottom portion of Table 1 shows the constituents and proportions of the additives. All proportions in Table 1 are in units of percent by weight.

As shown in Table 1, the base consists of oils, waters, and water soluble components. In the preferred embodiment, the base is an emulsion of oils, water and water soluble components. Generally, the base may include any emollients, lubricants, emulsifying agents, thickening agents, humectants, preservatives, antifungal agents, fragrances and wetting agents known in the art to be suitable for use in a moisturizing skin cream base. Also, any mixing methods known in the art to be suitable for mixing an oil and water emulsion for the purposes of forming a moisturizing skin cream may be used to mix the base ingredients.

Table 1 also shows the additives and their proportions. As shown in Table 1, the moisturizing skin cream consists of collagen, aloe, avocado oil and various forms of the Vitamins A, C, D and E. These vitamins are known to be vital to proper skin nutrition. Also shown in Table 1, the active ingredients include liposomes to ensure the vitamins are delivered to the proper skin depth.

TABLE 1

EXAMPLE COMPOSITIONS

| INGREDIENT NAME | I % | II % | III % | IV % | V % |
|---|---|---|---|---|---|
| BASE INGREDIENTS | | | | | |
| Deionized Water | 52.75 | 51.78 | 50.78 | 50.28 | 50.28 |
| Propylene Glycol | 5.00 | 5.00 | 5.00 | 5.00 | 4.00 |
| Methylparaben | 0.30 | 0.30 | 0.30 | 0.30 | 0.30 |
| Stearate, sold under the Trademarks MYRJ 52S and | 3.00 | 3.00 | 3.00 | 3.00 | 3.00 |

TABLE 1-continued

EXAMPLE COMPOSITIONS

| INGREDIENT NAME | I % | II % | III % | IV % | V % |
|---|---|---|---|---|---|
| PEG-8 STEARATE Panthenol, sold under the Trademark DL PANTHENOL 50% LIQUID | 2.00 | 2.00 | 2.00 | 2.00 | 2.00 |
| Stearyl Alcohol, sold under the Trademark STEARYL ALCOHOL NF | 3.00 | 3.00 | 3.00 | 3.00 | 3.00 |
| Glyceryl Stearate, sold under the Trademark WITCONOL-2400 | 3.00 | 3.00 | 3.00 | 3.00 | 3.00 |
| Lanolin, sold under the Trademark LANOLIN SUPRA CORONA | 2.00 | 2.00 | 2.00 | 2.00 | 2.00 |
| Mineral Oil, sold under the Trademark DRAKEOL 7 - CAR. MIN. OIL, where Car. Min. Oil is an abbreviation for Carnation Mineral Oil | 5.00 | 5.00 | 5.00 | 4.00 | 4.00 |
| Beeswax, sold under the Trademark WHITE BEESWAX 422 | 5.00 | 5.00 | 5.00 | 4.00 | 4.00 |
| Petrolatum, sold under the Trademark PETROLATUM SNOW WHITE | 10.00 | 9.50 | 9.00 | 9.00 | 8.00 |
| Dimethicone, sold under the Trademark RHODOSIL 47V350 | 1.00 | 1.00 | 1.00 | 1.00 | 1.00 |
| Butylparaben | .20 | .20 | .20 | .20 | .20 |
| Propylparaben | .02 | .02 | .02 | .02 | .02 |
| Fragrance, sold under the Trademark DRACENA GA 1091/A | 0.20 | 0.20 | 0.20 | 0.20 | 0.20 |
| TOTAL BASE ADDITIVES | 92.47 | 91.00 | 89.50 | 87.00 | 85.00 |
| Aloe Barbadensis Gel, sold under the Trademark ALOE VERA LIQUID 1 to 1 | 0.01 | 1.00 | 2.00 | 3.00 | 5.00 |
| Tocopheryl Acetate, sold under the Trademark VITAMIN E ACETATE C.G., where C.G. is an abbreviation for Cosmetic Grade | 1.00 | 1.00 | 1.00 | 1.00 | 1.00 |
| Vitamin A & D3 Liquid, sold under the Trademark VITAMIN A & D3 LIQUID [including the sub-Ingredients: 50% Corn Oil (also known as Zea Mays Oil), 45% Cholecalciferol, 5% Retinyl Palmitate] | 0.01 | 0.25 | 0.50 | 1.00 | 1.00 |
| Avocado Oil, also known as Persea Gratissima Oil, sold under the Trademark LIPOVOL A | 5.00 | 5.00 | 5.00 | 5.00 | 5.00 |
| Soluble Collagen, sold under the Trademark CLEARCOL SOL. COLLAGEN, where Sol. is an abbreviation for Soluble | 1.50 | 1.50 | 1.50 | 2.00 | 2.00 |
| Vitamin C & E Liposomes, sold under the Trademark VITAMIN C & E LIPOSOMES [including the sub-ingredients: 3% Phospholipids, 1% Tocophyl Acetate, 1% Ascorbyl Palmitate, and 95% Water] | 0.01 | 0.25 | 0.50 | 1.00 | 1.00 |
| TOTAL ADDITIVES | 7.53 | 9.00 | 10.50 | 13.00 | 15.00 |

For purposes of the present invention, the moisturizing skin cream can be applied daily. To apply, a generous amount is first placed on the fingertips or an appropriate delivery device such as a sponge or cloth. Next, the cream is dabbed onto the skin at the area to be treated. Finally, the cream is rubbed into the skin using the fingertips until the cream becomes transparent. Use of the skin cream immediately after washing and towel drying the skin is recommended for maximum moisturizing effect.

While the particular Moisturizing Skin Cream as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A dermatological composition for external use as a skin cream comprising:
   between about 0.01% and about 5.00% Aloe Barbadensis Gel;
   between about 0.9% and about 1.10% Tocopheryl Acetate;
   between about 0.01% and about 1.00% Vitamin A & D3 Liquid;
   between about 4.90% and about 5.10% Avocado Oil;
   between about 1.50% and about 2.00% Soluble Collagen;
   between about 0.01% and about 1.00% Vitamin C & E Liposomes; and
   a base for said composition comprising one or more compounds from the group consisting of emollients, lubricants, emulsifying agents, thickening agents, humectants, preservatives, antifungal agents, fragrances and wetting agents.

2. A dermatological composition as recited in claim 1 wherein said Aloe Barbadensis Gel concentration is about 0.01%, and wherein said Tocopheryl Acetate concentration is about 1.0%, and wherein said Vitamin A & D3 Liquid concentration is about 0.01%, and wherein said Avocado Oil concentration is about 5.00%, and wherein said Soluble Collagen concentration is about 1.50%, and wherein said Vitamin C & E Liposomes concentration is about 0.01%.

3. A dermatological composition as recited in claim 1 wherein said Aloe Barbadensis Gel concentration is about 1.00%, and wherein said Tocopheryl Acetate concentration is about 1.00%, and wherein said Vitamin A & D3 Liquid concentration is about 0.25%, and wherein said Avocado Oil concentration is about 5.00%, and wherein said Soluble Collagen concentration is about 1.50%, and wherein said Vitamin C & E Liposomes concentration is about 0.25%.

4. A dermatological composition as recited in claim 1 wherein said Aloe Barbadensis Gel concentration is about 2.00%, and wherein said Tocopheryl Acetate concentration is about 1.00%, and wherein said Vitamin A & D3 Liquid concentration is about 0.50%, and wherein said Avocado Oil concentration is about 5.00%, and wherein said Soluble Collagen concentration is about 1.50%, and wherein said Vitamin C & E Liposomes concentration is about 0.50%.

5. A dermatological composition as recited in claim 1 wherein said Aloe Barbadensis Gel concentration is about 3.00%, and wherein said Tocopheryl Acetate concentration is about 1.00, and wherein said Vitamin A & D3 Liquid concentration is about 1.00%, and wherein said Avocado Oil concentration is about 5.00%, and wherein said Soluble Collagen concentration is about 2.00%, and wherein said Vitamin C & E Liposomes concentration is about 1.00%.

6. A dermatological composition as recited in claim 1 wherein said Aloe Barbadensis Gel concentration is about 5.00%, and wherein said Tocopheryl Acetate concentration is about 1.00, and wherein said Vitamin A & D3 Liquid concentration is about 1.00%, and wherein said Avocado Oil concentration is about 5.00%, and wherein said Soluble Collagen concentration is about 2.00%, and wherein said Vitamin C & E Liposomes concentration is about 1.00%.

7. A method of using a dermatological composition for external use as a skin cream comprising the following steps:

mixing a composition consisting of between about 0.01% and about 5.00% Aloe Barbadensis Gel, and between about 0.9% and about 1.10% Tocopheryl Acetate, and between about 0.01% and about 1.00% Vitamin A & D3 Liquid, and between about 4.90% and about 5.10% Avocado Oil, and between about 1.50% and about 2.00% Soluble Collagen, and between about 0.01% and about 1.00% Vitamin C & E Liposomes, and a base for said composition comprising one or more compounds from the group consisting of emollients, lubricants, emulsifying agents, thickening agents, humectants, preservatives, antifungal agents, fragrances and wetting agents; and applying said composition to the skin.

\* \* \* \* \*